United States Patent
Kangawa et al.

(10) Patent No.: US 12,186,350 B2
(45) Date of Patent: Jan. 7, 2025

(54) ANTITUMOR EFFECT POTENTIATOR

(71) Applicants: NATIONAL CEREBRAL AND CARDIOVASCULAR CENTER, Suita (JP); KABUSHIKI KAISHA YAKULT HONSHA, Minato-ku (JP)

(72) Inventors: Kenji Kangawa, Suita (JP); Takashi Nojiri, Suita (JP); Motofumi Kumazoe, Suita (JP); Yasutake Tanaka, Suita (JP); Yoshiyuki Shishido, Minato-ku (JP); Takashi Asahara, Minato-ku (JP); Takahito Miura, Minato-ku (JP); Keisuke Taniguchi, Minato-ku (JP)

(73) Assignees: NATIONAL CEREBRAL AND CARDIOVASCULAR CENTER, Suita (JP); KABUSHIKI KAISHA YAKULT HONSHA, Minato-ku (JP)

( * ) Notice: Subject to any disclaimer, the term of this patent is extended or adjusted under 35 U.S.C. 154(b) by 426 days.

(21) Appl. No.: 17/279,322

(22) PCT Filed: Sep. 25, 2019

(86) PCT No.: PCT/JP2019/037623
§ 371 (c)(1),
(2) Date: Mar. 24, 2021

(87) PCT Pub. No.: WO2020/067170
PCT Pub. Date: Apr. 2, 2020

(65) Prior Publication Data
US 2022/0000949 A1 Jan. 6, 2022

(30) Foreign Application Priority Data

Sep. 25, 2018 (JP) ................. 2018-178746

(51) Int. Cl.
*A61K 35/747* (2015.01)
*A61K 31/702* (2006.01)
(Continued)

(52) U.S. Cl.
CPC .......... *A61K 35/747* (2013.01); *A61K 31/702* (2013.01); *A61K 35/745* (2013.01);
(Continued)

(58) Field of Classification Search
None
See application file for complete search history.

(56) References Cited

U.S. PATENT DOCUMENTS

2006/0110383 A1 5/2006 Honjo et al.
2012/0329059 A1 12/2012 Sako et al.
(Continued)

FOREIGN PATENT DOCUMENTS

CN 106110322 A 11/2016
CN 106617092 A 5/2017
(Continued)

OTHER PUBLICATIONS

De Graaff et al., Exp. Opin. Biologic. Ther., 18(10):1023-1040 (2018) (Year: 2018).*

(Continued)

*Primary Examiner* — Thomas J. Visone
(74) *Attorney, Agent, or Firm* — Oblon, McClelland, Maier & Neustadt, L.L.P.

(57) ABSTRACT

An activator suitable for immune response in tumor immunotherapy using an immune checkpoint inhibitor. An agent suitable for potentiating an antitumor effect of an immune checkpoint inhibitor, may contain a probiotic and a prebiotic as active ingredients.

2 Claims, 5 Drawing Sheets

(51) Int. Cl.
*A61K 35/00* (2006.01)
*A61K 35/745* (2015.01)
*A61P 35/00* (2006.01)
*C07K 16/28* (2006.01)

(52) U.S. Cl.
CPC .......... *A61P 35/00* (2018.01); *C07K 16/2818* (2013.01); *C07K 16/2827* (2013.01); *A61K 2035/115* (2013.01)

(56) References Cited

U.S. PATENT DOCUMENTS

| | | | |
|---|---|---|---|
| 2015/0307856 A1 | 10/2015 | Bruno-Barcena et al. | |
| 2016/0194675 A1 | 7/2016 | Benjamins et al. | |
| 2016/0354416 A1 | 12/2016 | Gajewski et al. | |
| 2017/0340683 A1* | 11/2017 | Petri | A61K 35/742 |
| 2018/0015131 A1* | 1/2018 | Gajewski | A61P 43/00 |
| 2019/0037902 A1* | 2/2019 | Fischer | C12N 1/205 |
| 2019/0183942 A1 | 6/2019 | Gajewski et al. | |
| 2020/0046781 A1* | 2/2020 | Friedland | A61P 25/16 |
| 2020/0121739 A1* | 4/2020 | Goodman | A61K 39/001164 |
| 2020/0129570 A1* | 4/2020 | Frankel | C07K 16/2818 |

FOREIGN PATENT DOCUMENTS

| | | | | |
|---|---|---|---|---|
| CN | 107847530 A | | 3/2018 | |
| EP | 2 471 544 A1 | | 7/2012 | |
| EP | 2 522 355 A1 | | 11/2012 | |
| JP | 2002-241292 A | | 8/2002 | |
| JP | 2015-536155 A | | 12/2015 | |
| JP | 5885764 B2 | | 3/2016 | |
| JP | 2016-529912 A | | 9/2016 | |
| JP | 2018-505842 A1 | | 3/2018 | |
| JP | 2018-521013 A | | 8/2018 | |
| WO | WO-2011105335 A1 * | | 9/2011 | A23C 9/1234 |
| WO | WO-2014142186 A1 * | | 9/2014 | C07K 14/195 |

OTHER PUBLICATIONS

Geier et al., Cancer Biol. Ther., 5(10):1265-1269 (2006) (Year: 2006).*
Office Action issued Jun. 6, 2023, in corresponding Japanese Patent Application No. 2020-549294 (with English Translation), 6 pages.
Extended European Search Report issued Apr. 20, 2022 in European Patent Application 19864575.6, 11 pages.
Kan Shida, et al., "Probiotics as Efficient Immunopotentiators: Translational Role in Cancer Prevention" Internet Citation, Retrieved from the Internet: https://www.ncbi.nlm.nih.gov/pubmed/24434333, XP002787061, Nov. 1, 2013, 8 pages.
Gen Sugawara, et al., "Perioperative Synbiotic Treatment to Prevent Postoperative Infectious Complications in Biliary Cancer Surgery: A Randomized Controlled Trial" Annals of Surgery, vol. 244, No. 5, XP055909928, Nov. 1, 2006, pp. 706-714.
Bertrand Routy, et al., "Gut Microbiome Influences Efficacy of PD-1-Based Immunotherapy Against Epithelial Tumors" Science, vol. 359, No. 6371, XP055554928, Jan. 5, 2018, pp. 91-97.
Jose M. Bruno-Barcena, et al., "Galacto-Oligosaccharides and Colorectal Cancer: Feeding our Intestinal Probiome" Journal of Functional Foods, vol. 12, XP055910589, Jan. 1, 2015, pp. 92-108.
International Search Report issued on Nov. 12, 2019 in PCT/JP2019/037623 filed on Sep. 25, 2019, 3 pages.
Asahara, T., "The usefulness of synbiotics in the perioperative period," Annual report of the Yakult Institute for Microbiological Research, No. 35, 2017, pp. 11-19.
Combined Chinese Office Action and Search Report issued Sep. 6, 2023 in Chinese Application 201980062321.5, (with unedited computer-generated English translation), 40 pages.

* cited by examiner

ANTITUMOR EFFECT POTENTIATOR

TECHNICAL FIELD

The present invention relates to an agent for potentiating an antitumor effect and an agent for activating tumor immunity which activate the tumor immune response to enhance the antitumor effect by the tumor immune response.

BACKGROUND ART

Tumor immunotherapy is a therapy which suppresses the progression of cancer or treats cancer by acting on the immune surveillance system inherent in the cancer patient and strengthening the immune system against cancer. In recent years, it has been clarified that cancer cells themselves have a system through which they evade the immune surveillance system in the development of cancer, and immune checkpoint molecules such as CTLA-4 and PD-1 or PD-L1 which is a ligand thereof are known as molecules used in such an evasion system. It has been reported that immune checkpoint inhibitors which inhibit the functions of these immune checkpoint molecules are extremely useful for strengthening the immune system against cancer (Patent Literature 1).

Regulatory T cells (Treg) which are responsible for the suppressive control of the immune response suppress the induction of the immune response during disease such as cancer or diseases caused by infectious bacteria. Therefore, various attempts have been made in tumor immunotherapy to control the function of regulatory T cells.

However, there are cancer patients on which a sufficient therapeutic effect cannot be exerted even by activating the immune system using such an immune checkpoint inhibitor or the like, and thus further development of a therapeutic method is required.

Meanwhile, it has been revealed that lactic acid bacteria typified by bacteria of the genus *Lactobacillus* or the like and bacteria of the genus *Bifidobacterium* have various effects such as improvement of intestinal microbiota, improvement of fecal environment, improvement of intestinal functions, infection protection, and immune activation. These bacteria are thought to contribute to human health through improvement of the intestinal environment, and are so-called probiotics.

CITATION LIST

Patent Literature

Patent Literature 1: JP-B-5885764

SUMMARY OF INVENTION

Technical Problem

The present invention relates to provision of a new method for activating the immune response in tumor immunotherapy using an immune checkpoint inhibitor.

Solution to Problem

As a result of diligent studies in order to solve the above problems, the inventors have found that the antitumor effect is remarkably enhanced, and further tumor immunity is activated, when a combination of probiotics such as bacteria of the genus *Lactobacillus* and bacteria of the genus *Bifidobacterium* and prebiotics such as a galactooligosaccharide is used in combination with an immune checkpoint inhibitor.

That is, the present invention relates to the following 1) to 19).

1) An agent for potentiating an antitumor effect of an immune checkpoint inhibitor, comprising a probiotic and a prebiotic as active ingredients.
2) The agent for potentiating the antitumor effect according to 1), wherein the probiotic is one or more selected from the group consisting of bacteria of the genus *Lactobacillus* and bacteria of the genus *Bifidobacterium*.
3) The agent for potentiating the antitumor effect according to 1) or 2), wherein the probiotic is one or more selected from the group consisting of *Lactobacillus casei* and *Bifidobacterium breve*.
4) The agent for potentiating the antitumor effect according to any one of 1) to 3), wherein the probiotic is one or more selected from the group consisting of *Lactobacillus casei* YIT9029 (FERM BP-1366) and *Bifidobacterium breve* YIT12272 (FERM BP-11320).
5) The agent for potentiating the antitumor effect according to any one of 1) to 4), wherein the prebiotic is a galactooligosaccharide.
6) The agent for potentiating the antitumor effect according to any one of 1) to 5), wherein the prebiotic is a galactooligosaccharide comprising β-1,4 galactosyllactose as a main ingredient.
7) The agent for potentiating the antitumor effect according to any one of 1) to 6), wherein the immune checkpoint inhibitor is one or more selected from the group consisting of an anti-PD-1 antibody, an anti-PD-L1 antibody, and a PD-1 antagonist.
8) An agent for activating tumor immunity, comprising a probiotic, a prebiotic, and an immune checkpoint inhibitor as active ingredients.
9) The agent for activating tumor immunity according to 8), wherein the tumor immunity is activated by reversing immunosuppressive state mediated by regulatory T cells and/or activating NK cells.
10) A medicament, comprising a combination of a probiotic, a prebiotic, and an immune checkpoint inhibitor.
11) A pharmaceutical composition for use in combination with an immune checkpoint inhibitor, comprising a probiotic and a prebiotic.
12) Use of a probiotic and a prebiotic, for producing an agent for potentiating an antitumor effect of an immune checkpoint inhibitor.
13) Use of a probiotic, a prebiotic, and an immune checkpoint inhibitor, for producing an agent for activating tumor immunity.
14) Use of a combination of a probiotic, a prebiotic, and an immune checkpoint inhibitor for producing a medicament.
15) A probiotic and a prebiotic for use in potentiating an antitumor effect of an immune checkpoint inhibitor.
16) A probiotic, a prebiotic, and an immune checkpoint inhibitor for use in activating tumor immunity.
17) A combination of a probiotic, a prebiotic, and an immune checkpoint inhibitor for use in a medicament.
18) A method for potentiating an antitumor effect of an immune checkpoint inhibitor, comprising administering a probiotic and a prebiotic to a subject in need thereof.
19) A method for activating tumor immunity, comprising administering a probiotic, a prebiotic, and an immune checkpoint inhibitor to a subject in need thereof.

Effects of Invention

The present invention can activate tumor immunity and enables the suppression of the progression and recurrence of cancer or the treatment of the cancer.

DESCRIPTION OF EMBODIMENTS

Figure 1:
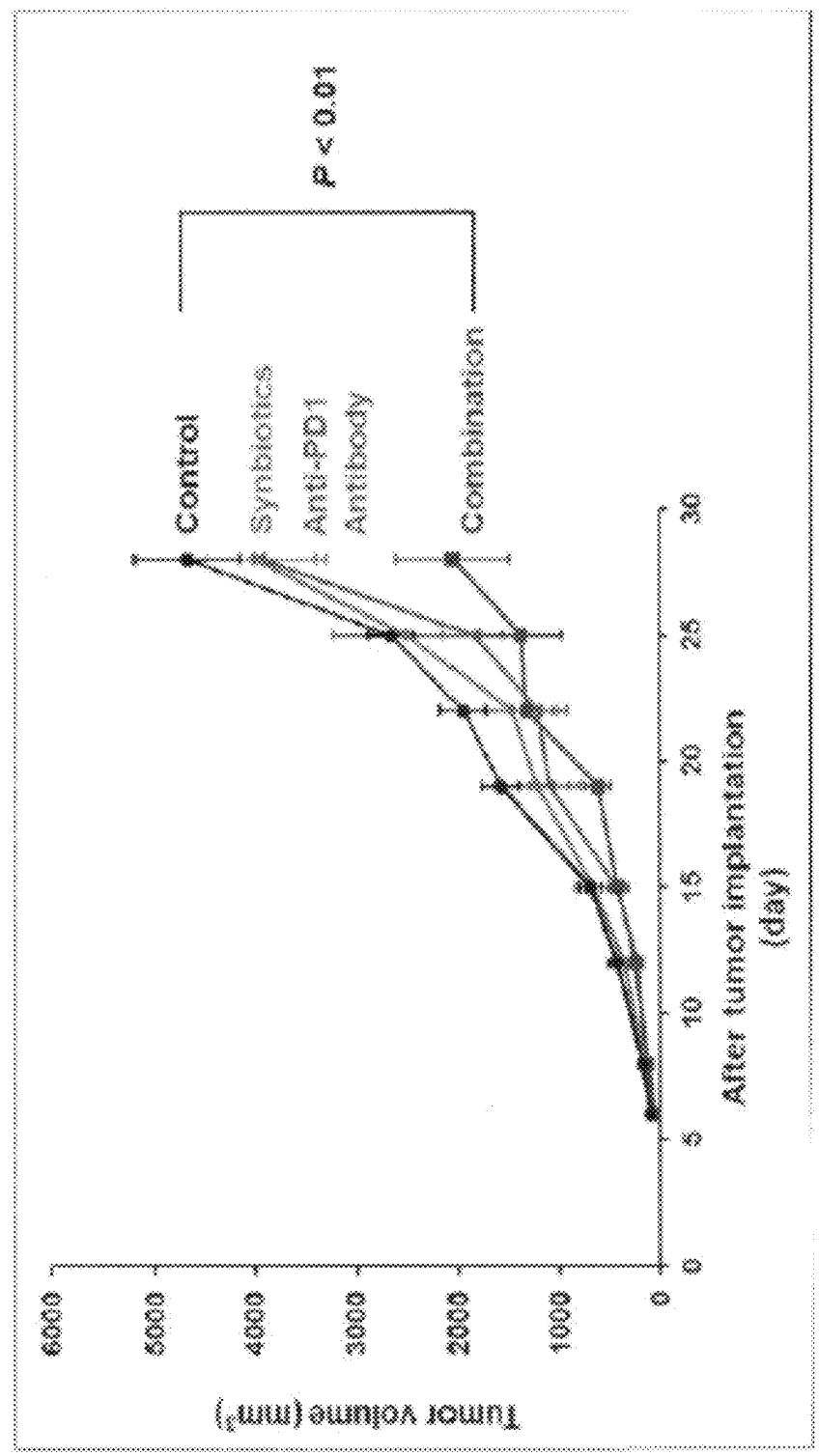
FIG. 1 shows the antitumor action of synbiotics in combination with an immune checkpoint inhibitor.

In the present invention, the term "probiotics" refers to live microorganisms which cause a beneficial action on the health of the host when taken in appropriate amounts. The term "prebiotics" refers to those which serve as "baits" of bifidobacteria and lactic acid bacteria to beneficially act by proliferating these bacteria.

Specifically, examples of the probiotics in the present invention include one or more microorganisms selected from the group consisting of bacteria of the genus *Lactobacillus*, bacteria of the genus *Bifidobacterium*, bacteria of the genus *Streptococcus*, and bacteria of the genus *Lactococcus*.

Examples of the bacteria of the genus *Lactobacillus* include *Lactobacillus casei* (*L. casei*), *Lactobacillus acidophilus* (*L. acidophilus*), *Lactobacillus plantarum* (*L. plantarum*), *Lactobacillus buchneri* (*L. buchneri*), *Lactobacillus gallinarum* (*L. gallinarum*), *Lactobacillus amylovorus* (*L. amylovorus*), *Lactobacillus brevis* (*L. brevis*), *Lactobacillus rhamnosus* (*L. rhamnosus*), *Lactobacillus kefir* (*L. kefir*), *Lactobacillus curvatus* (*L. curvatus*), *Lactobacillus zeae* (*L. zeae*), *Lactobacillus helveticus* (*L. helveticus*), *Lactobacillus salivarius* (*L. salivalius*), *Lactobacillus gasseri* (*L. gasseri*), *Lactobacillus fermentum* (*L. fermentum*), *Lactobacillus reuteri* (*L. reuteri*), *Lactobacillus crispatus* (*L. crispatus*), *Lactobacillus delbrueckii* subsp. *bulgaricus* (*L. delbrueckii* subsp. *bulgaricus*), *Lactobacillus delbrueckii* subsp. *delbrueckii* (*L. delbrueckii* subsp. *delbrueckii*), and *Lactobacillus johnsonii* (*L. johnsonii*).

Among these, from the viewpoint of potentiating an antitumor effect, *Lactobacillus casei* and *Lactobacillus acidophilus* are preferable, and *Lactobacillus casei* YIT 9018 (FERM BP-665), *Lactobacillus casei* YIT 9029 (FERM BP-1366), *Lactobacillus casei* YIT 10003 (FERM BP-7707), and *Lactobacillus acidophilus* YIT 0198 are more preferable, and *Lactobacillus casei* YIT 9029 (FERM BP-1366) is even more preferable. Strain of *Lactobacillus casei* YIT 9029 have been deposited under the terms of the Budapest Treaty with the National Institute of Technology and Evaluation, #120, 2-5-8, Kazusakamatari, Kisarazu-shi, Chiba, 292-0818, Japan, on Feb. 16, 2010, and have been granted the accession number FERM BP-1366.

Examples of the bacteria of the genus *Bifidobacterium* include *Bifidobacterium breve*, *Bifidobacterium longum* (*B. longum*), *Bifidobacterium bifidum* (*B. bifidum*), *Bifidobacterium animalis* (*B. animalis*), *Bifidobacterium suis* (*B. suis*), *Bifidobacterium infantis* (*B. infantis*), *Bifidobacterium adolescentis* (*B. adolescentis*), *Bifidobacterium catenulatum* (*B. catenulatum*), *Bifidobacterium pseudocatenulatum* (*B. pseudocatenulatum*), *Bifidobacterium lactis* (*B. lactis*), and *Bifidobacterium globosum* (*B. globosum*).

Among these, from the viewpoint of potentiating an antitumor effect, *Bifidobacterium breve*, *Bifidobacterium bifidum*, and *Bifidobacterium pseudocatenulatum* are preferable, and *Bifidobacterium breve* YIT12272 (FERM BP-11320), *Bifidobacterium breve* YIT10001 (FERM BP-8205), and *Bifidobacterium bifidum* YIT 10347 (FERM BP-10613) are more preferable. Strain of *Bifidobacterium breve* YIT12272 have been deposited under the terms of the Budapest Treaty with the National Institute of Technology and Evaluation, #120, 2-5-8, Kazusakamatari, Kisarazu-shi, Chiba, 292-0818, Japan, on Feb. 16, 2010, and have been granted the accession number FERM BP-11320.

Examples of the bacteria of the genus *Streptococcus* include *Streptococcus thermophilus* and *Streptococcus lactis*.

Among these, from the viewpoint of potentiating an antitumor effect, *Streptococcus thermophilus* is preferable, and *Streptococcus thermophilus* YIT 2021 (FERM BP-7537) is more preferable.

Examples of the bacteria of the genus *Lactococcus* include *Lactococcus lactis* subsp. *lactis*, *Lactococcus lactis* subsp. *cremoris*, *Lactococcus plantarum*, and *Lactococcus raffinolactis*.

Among these, from the viewpoint of potentiating an antitumor effect, *Lactococcus lactis* is preferable, and *Lactococcus lactis* YIT 2027 (FERM BP-6224) is more preferable.

The prebiotics in the present invention are preferably substances which cause a beneficial action on the host preferably by acting on the probiotics of the present invention. Specifically, examples thereof include one or more selected from the group consisting of oligosaccharides such as galactooligosaccharides, fructooligosaccharides, lactose fructose oligosaccharides, isomaltooligosaccharides, soybean oligosaccharides, nigerooligosaccharides, gentiooligosaccharides, pectin oligosaccharides, and cyclodextrins; and dietary fibers such as polydextroses, inulins, germinated barley, inulins, indigestible dextrins, and resistant starch.

In the present invention, the prebiotics are preferably galactooligosaccharides, from the viewpoint of potentiating an antitumor effect.

Here, galactooligosaccharides generally refer to oligosaccharides having at least one or more galactose residues in the molecule, and examples thereof include sugars composed of 2 to 9, preferably 3 to 4 monosaccharides. Examples of the galactooligosaccharides include those in which galactose is linked via a β1-2 bond, those in which galactose is linked via a β1-3 bond, those in which galactose is linked via a β1-4 bond, and those in which galactose is linked via a β1-6 bond, and galactooligosaccharides in which galactose is linked via a β1-4 bond and those in which galactose is linked via a β1-6 bond are particularly preferable.

Examples of more preferred galactooligosaccharides include β-1,4 galactosyllactose (Galβ1-4Galβ1-4Glc), β-1,6 galactosyllactose (Galβ1-6Galβ1-4Glc), and β-1,3 galactosyllactose (Galβ1-3Galβ1-4Glc). From the viewpoint of potentiating an antitumor effect, galactooligosaccharides containing β-1,4 galactosyllactose as the main component are more preferable. For example, Oligomate 55N (Yakult Pharmaceutical Industry Co., Ltd., with a content of β-1,4 galactosyllactose in solid content of 18.5%) can be used.

In the present invention, probiotics and prebiotics are used in combination as synbiotics. The synbiotics are preferably used as a formulation (intestinal bacteria formulation) prepared by mixing the two.

The content of probiotics in the formulation is not specifically limited but is, for example, $0.1 \times 10^{11}$ to $100 \times 10^{11}$ CFU (colony forming units), and preferably $1 \times 10^{11}$ to $10 \times 10^{11}$ CFU in 100 g of the formulation.

The content ratio of probiotics to prebiotics in the formulation is, for example, $0.01 \times 10^{11}$ to $20 \times 10^{11}$ CFU, and preferably $0.2 \times 10^{11}$ to $2 \times 10^{11}$ CFU of probiotics, with respect to 1 g of the total mass of prebiotics.

The content of prebiotics in the formulation is not specifically limited but is 0.5 to 40 mass %, preferably 2 to 10 mass %, and more preferably 3 to 6 mass %, in the formulation.

The synbiotics may contain other ingredients as long as the effects of the present invention are not impaired. Examples of the other ingredients include minerals such as calcium, magnesium, zinc, iron, and dolomite, and salts thereof; acids such as citric acid, malic acid, ascorbic acid, lactic acid, acetic acid, and amino acids; additives such as collagen, chondroitin sulfate, hydroxyproline, flavones, flavonols, isoflavones, anthocyans, catechins, and proanthocyanidins; and various vitamins such as vitamin A, vitamin Bs, vitamin C, vitamin E, vitamin Ds, vitamin Ks, beta carotene, retinoic acid, and folic acid. One of these can be used alone, or two or more of these can be used in combination.

The administration form of synbiotics is not specifically limited, but examples thereof include forms enabling oral administration and forms enabling enteral administration. The form of oral administration is preferable.

Examples of the form of oral administration include tablets (including sugar-coated tablets, enteric coated tablets, and buccal tablets), powders, capsules (including enteric capsules and soft capsules), granules (including coated granules), pills, lozenges, encapsulated liposomes, liquid agents, and pharmaceutical formulations such as sustained-release formulations of these. Examples of the form may also include foods (e.g., beverages such as soft drinks, carbonated beverages, nutritional beverages, fruit juice beverages, and lactic acid bacteria beverages; milk products such as processed milk, milk beverages, fermented milk, and butter; and functional foods such as health supplements).

For formulation, carriers and additives such as excipients (e.g., lactose, glucose, white sugar, mannitol, potato starch, corn starch, calcium carbonate, calcium phosphate, calcium sulfate, and crystalline cellulose), binders (e.g., starch, gelatin, glucose, galactose, polyvinyl alcohol, polyvinyl ether, polyvinylpyrrolidone, hydroxypropyl cellulose, ethyl cellulose, methyl cellulose, and carboxymethyl cellulose), disintegrants (e.g., starch, agar, gelatin, sodium carboxymethyl cellulose, calcium carboxymethyl cellulose, crystalline cellulose, calcium carbonate, sodium bicarbonate, and sodium alginate), lubricants (e.g., magnesium stearate, hydrogenated vegetable oil, and macrogol), stabilizers, flavoring agents, diluents, surfactants, and solvents, which are generally used in ordinary pharmaceutical formulations can be used.

In the present invention, the term "immune checkpoint inhibitors" means molecules which inhibit the functions of the immune checkpoint molecules such as CTLA-4 and PD-1 or PD-L1 which is a ligand thereof.

Examples of the immune checkpoint inhibitors include an anti-PD-1 antibody (e.g., Nivolumab and Pembrolizumab), an anti-PD-L1 antibody (e.g., Atezolizumab, Avelumab, and Durvalumab), a PD-1 antagonist (e.g., AUNP-12), an anti-CTLA-4 antibody (e.g., Ipilimumab and Tremelimumab), and an anti-LAG-3 antibody (e.g., BMS-986016 and LAG525).

Among these, from the viewpoint of potentiating an antitumor effect, an anti-PD-1 antibody, an anti-PD-L1 antibody, and a PD-1 antagonist are preferable, and anti-PD-1 antibody is more preferable.

As described in Examples below, a combination of probiotics and prebiotics according to the present invention, when used in combination with an immune checkpoint inhibitor, potentiates the antitumor effect obtained by the immune checkpoint inhibitor. Accordingly, the combination of probiotics and prebiotics can serve as an agent for potentiating the antitumor effect of the immune checkpoint inhibitor.

Use of probiotic and prebiotic, and an immune checkpoint inhibitor in combination suppresses the tumor immunosuppressive system, for example, by activating Th1 cells ($CD3^+$/$CD4^+$/IFN-$\gamma^+$ and $CD3^+$/$CD8^+$/IFN-$\gamma^+$) and NK cells and suppressing the expression and functions of regulatory T cells (Treg), myeloid-derived suppressor cells (MDSC), and immunosuppressive cytokines (TGF-β). Accordingly, the combination of probiotics and prebiotics, and an immune checkpoint inhibitor can serve as an agent for activating tumor immunity.

The agent for potentiating the antitumor effect of the immune checkpoint inhibitor and the agent for activating tumor immunity can be used for suppressing the progression and recurrence of cancer or treating cancer.

The agent for potentiating the antitumor effect of the immune checkpoint inhibitor and the agent for activating tumor immunity of the present invention can also reduce the dose and adverse effects of the immune checkpoint inhibitor.

The cancer targeted by the agent for potentiating the antitumor effect of the immune checkpoint inhibitor or the agent for activating tumor immunity of the present invention is not specifically limited, and any solid cancers and any blood cancers are included. Examples thereof include head and neck cancer, esophageal cancer, stomach cancer, colorectal cancer, liver cancer, biliary/bile duct cancer, pancreatic cancer, lung cancer, breast cancer, ovarian cancer, bladder cancer, prostate cancer, testicular cancer, bones/soft tissue sarcoma, malignant lymphoma, leukemia, cervical cancer, skin cancer, and brain tumor. Among these, cancers for which tumor immunotherapy using an immune checkpoint inhibitor is effective are preferable.

The probiotics and prebiotics of the present invention may be administered simultaneously with the immune checkpoint inhibitor, the probiotics and prebiotics may be administered first, and then the immune checkpoint inhibitor may be administered after the aforementioned administration, or the immune checkpoint inhibitor may be administered first, and then the probiotics and prebiotics may be administered thereafter.

The administration form of the probiotics and prebiotics may be the same as or different from that of the immune checkpoint inhibitor, and they may be administered in the respective suitable forms. The probiotics and prebiotics, and the immune checkpoint inhibitor can be one pharmaceutical formulation as a kit combining these.

In the agent for potentiating the antitumor effect of the immune checkpoint inhibitor or the agent for activating tumor immunity of the present invention, the doses of the probiotics and prebiotics differ depending on the age, body weight, symptoms, therapeutic effect, administration method, treatment time, and the like, but are generally a dose ranging from $3 \times 10^7$ to $3 \times 10^{11}$ CFU, preferably from $3 \times 10^8$ to $3 \times 10^{10}$ CFU, in terms of probiotics, and from 1 to 10 g, preferably from 3 to 9 g, in terms of prebiotics, per day for an adult, preferably once to several times a day.

The dose of the immune checkpoint inhibitor can be appropriately selected with reference to the dose which is clinically used. Any two or more immune checkpoint inhibitors may be administered in combination.

EXAMPLES

The present invention will be described further in detail by way of the following examples, but the scope of the present invention is not limited to these examples.
<Examined Items>
1) Probiotics
The strains used were *Lactobacillus casei* YIT9029 (FERM BP-1366) and *Bifidobacterium breve* YIT12272 (FERM BP-11320).
2) Prebiotics
Galactooligosaccharides containing β-1,4 galactosyllactose as the main ingredient
3) Synbiotics
   1 mL of GOS (100 mg/1 mL), 0.5 mL ($20 \times 10^8$ CFU/1 mL) of *Lactobacillus casei* YIT9029, and 0.5 mL ($20 \times 10^8$ CFU/1 mL) of *Bifidobacterium breve* YIT12272 were mixed.
4) Anti-PD-1 Antibody
   "Anti-PD1 (J43) Hamster IgG ms" (Bio X Cell) (control antibody "IgG Isotype Hamster IgG ms" (Bio X Cell))

Example 1: Antitumor Action by In-Vivo Use of Synbiotics in Combination with Immune Checkpoint Inhibitor Mouse colon cancer cell line MC38 cells were transplanted into 7-week-old male C57BL/6NCrSlc mice to produce cell line-transplanted model mice. They were divided into a control (Vehicle) group, a synbiotics-administered group, an anti-PD-1 antibody-administered group, and a synbiotics+anti-PD-1 antibody-administered group [n=10 (Vehicle group), n=5 (synbiotics-administered group and anti-PD-1 antibody-administered group), and n=6 (synbiotics+anti-PD-1 antibody-administered group)].

The synbiotics were orally administered at 0.2 mL/mouse once per day daily for 28 days after the transplantation, and the anti-PD-1 antibody was intraperitoneally administered from Day 7 after the tumor transplantation initially at 20 mg/kg and thereafter 10 mg/kg from the second to fourth time every 7 days.

The tumor volume was measured with calipers (Tukey-Kramer test).

The tumor volume was calculated by measuring the major axis and the minor axis of the tumor, and using the formula $\{(\text{major axis}) \times (\text{minor axis})^2\}/2$.

FIG. 1 shows the results. FIG. 1 demonstrated that the tumor volume in the group receiving a combination of anti-PD-1 antibody and synbiotics was significantly small. Meanwhile, no significant reduction in tumor volume was observed in the group receiving each of the two drugs alone. Further, the tumor size in the single use was larger than that at the midpoint of the Vehicle group and the synbiotics+anti-PD-1 antibody-administered group. Thus, the effect of the combination was different from a mere additive effect. Therefore, it can be determined that a tumor growth inhibitory action was exerted specifically when the anti-PD-1 antibody and the synbiotics were used in combination.

Example 2: Influence of In-Vivo Use of Synbiotics in Combination with Immune Checkpoint on Immune Cells Mouse colon cancer cell line MC38 cells were transplanted into 7-week-old male C57BL/6NCrSlc mice to produce cell line-transplanted model mice. They were divided into a control (Vehicle) group, a synbiotics-administered group, an anti-PD-1 antibody-administered group, and a synbiotics+anti-PD-1 antibody-administered group.

The synbiotics were orally administered at 0.2 mL/mouse once per day daily for 28 days after the transplantation, and the anti-PD-1 antibody was intraperitoneally administered from Day 7 after the tumor transplantation initially at 20 mg/kg and thereafter 10 mg/kg from the second to fourth time every 7 days.

At the time of dissection, each tissue (spleen and tumor) was collected, and the cells were separated into a single cell state. The isolated cells were labeled with marker protein-specific antibodies of various immune cells and identified by a flow cytometer. From the identification data, the cell proportion of each cell population of Th1 cells ($CD3^+/CD4^+/IFN-\gamma^+$ and $CD3^+/CD8^+/IFN-\gamma^+$) and Tregs was measured [n=8 (Vehicle group), n=5 (synbiotics-administered group and anti-PD-1 antibody-administered group), and n=6 (synbiotics+anti-PD-1 antibody-administered group), Student's t test].

Figure 2:
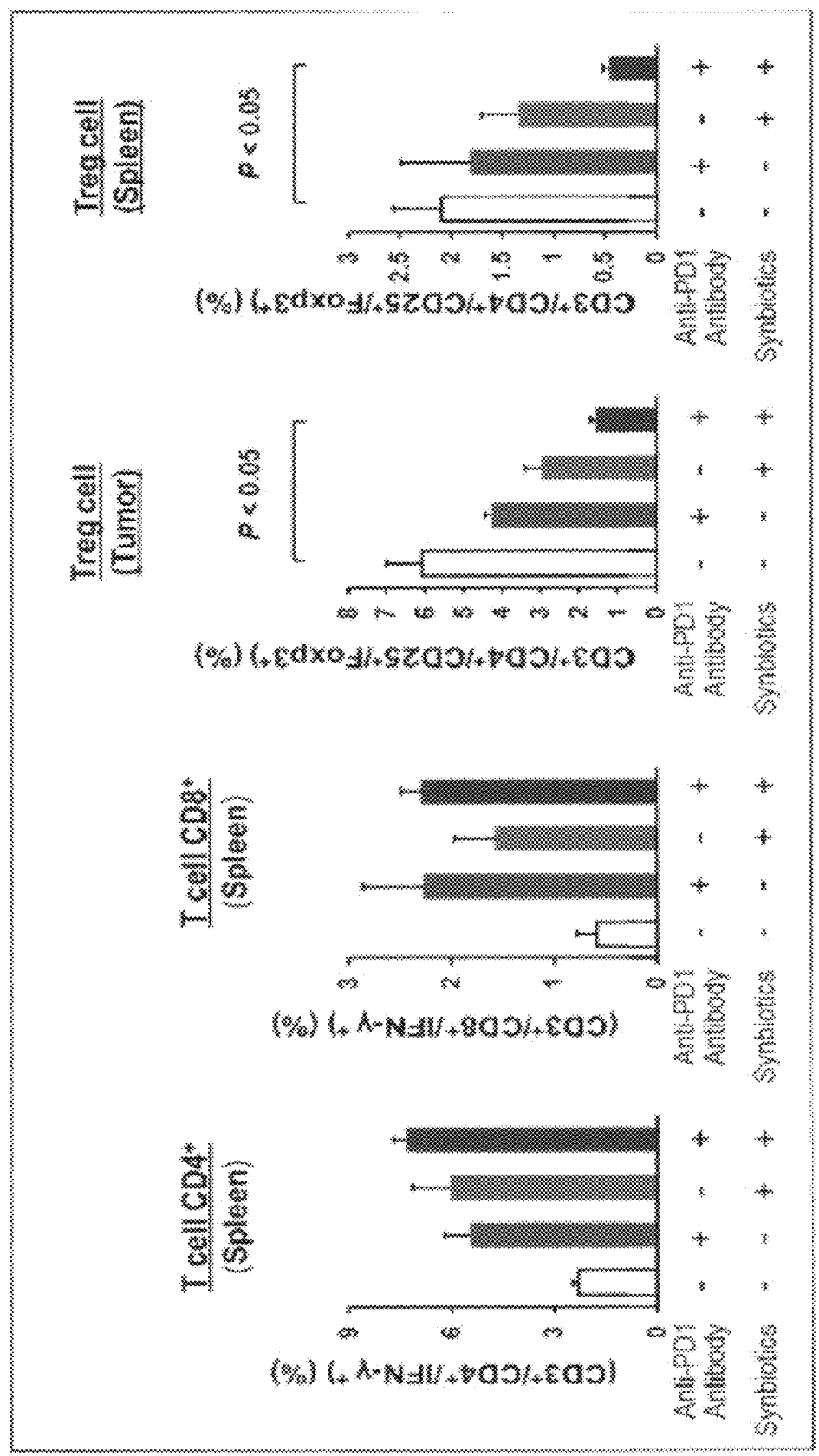
FIG. 2 shows the influence of synbiotics in combination with an immune checkpoint inhibitor on immune cells.

FIG. 2 shows the results. From FIG. 2, it was confirmed that the number of Tregs which suppress the activity of surrounding immune cells significantly decreased only in the synbiotics+anti-PD-1 antibody-administered group. Since Tregs were also utilized as an anti-immune mechanism of tumor cells, it can be inferred from this result that the anti-immune defense of the tumor was suppressed by the use of both formulations in combination. Meanwhile, since the number of T cells activated in the spleen (which were positive for activation markers CD8 and CD4) did not increase specifically in the synbiotics+anti-PD-1 antibody-administered group, it was suggested that the effect by the combined use was mediated by activation of immune cells.

Example 3: Influence of In-Vivo Use of Synbiotics in Combination with Immune Checkpoint Inhibitor on Regulatory T Cells (Tregs) in Small Intestine Mouse colon cancer cell line MC38 cells were transplanted into 7-week-old male C57BL/6NCrSlc mice to produce cell line-transplanted model mice. They were divided into a control (Vehicle) group, a synbiotics-administered group, an anti-PD-1 antibody-administered group, and a synbiotics+anti-PD-1 antibody-administered group [n=10 (Vehicle group), n=5 (synbiotics-administered group and anti-PD-1 antibody-administered group), and n=6 (synbiotics+anti-PD-1 antibody-administered group)].

The synbiotics were orally administered at 0.2 mL/mouse once per day daily for 28 days after the transplantation, and the anti-PD-1 antibody was intraperitoneally administered from Day 7 after the tumor transplantation initially at 20 mg/kg and thereafter 10 mg/kg from the second to fourth time every 7 days.

At the time of dissection, the small intestine was collected and Tregs were evaluated by real-time PCR using FOXP3 as an index (Mann Whitney U test).

Figure 3:
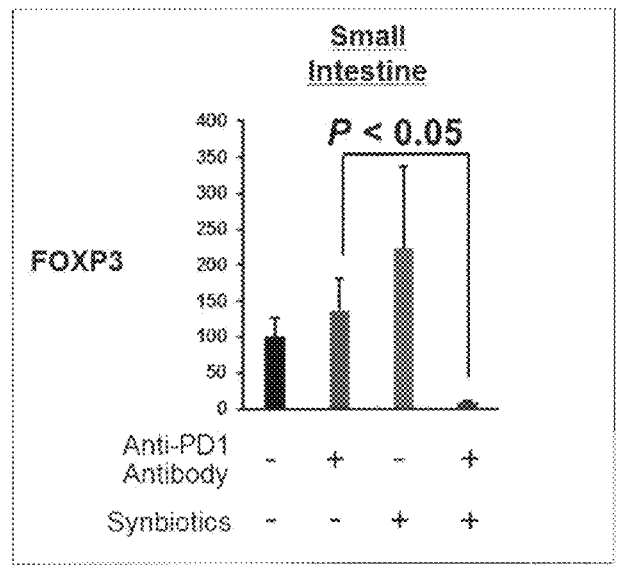
FIG. 3 shows the influence of synbiotics in combination with an immune checkpoint inhibitor on regulatory T cells (Tregs).

FIG. 3 shows the results. FIG. 3 demonstrated that the expression level of the FOXP3 gene which is a master transcription factor in Tregs decreased significantly in the synbiotics+anti-PD-1 antibody-administered group. This result supports the aforementioned decrease of the number of Tregs.

Example 4: Influence of In-Vivo Use of Synbiotics in Combination with Immune Checkpoint Inhibitor on Systemic Immunosuppressive State Mouse colon cancer cell line MC38 cells were transplanted into 7-week-old male C57BL/6NCrSlc mice to produce cell line-transplanted model mice. They were divided into a control (Vehicle) group, a synbiotics-administered group, an anti-PD-1 antibody-administered group, and a synbiotics+anti-PD-1 antibody-administered group [n=10 (Vehicle group), n=5 (synbiotics-administered group and anti-PD-1 antibody-administered group), and n=6 (synbiotics+anti-PD-1 antibody-administered group)].

The synbiotics were orally administered at 0.2 mL/mouse once per day daily for 28 days after the transplantation, and the anti-PD-1 antibody was intraperitoneally administered from Day 7 after the tumor transplantation initially at 20 mg/kg and thereafter 10 mg/kg from the second to fourth time every 7 days.

At the time of dissection, each tissue (small intestine and Peyer's patch) was collected, and the immunosuppressive state was evaluated by real-time PCR using TGFβ as an index (Mann Whitney U test).

Figure 4:
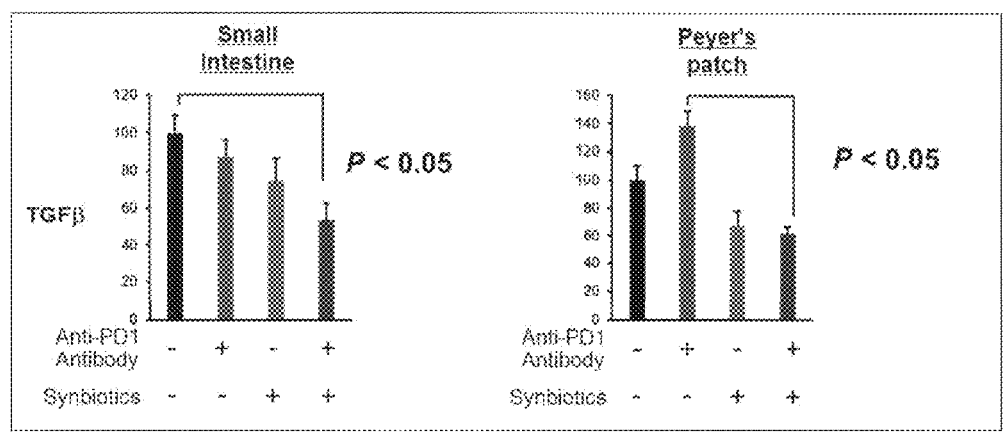
FIG. 4 shows the influence of synbiotics in combination with an immune checkpoint inhibitor on the immunosuppressive state.

FIG. 4 shows the results. FIG. 4 demonstrated that TGFβ is an immunosuppressive cytokine and is induced by substances derived from enteric bacteria. FIG. 4 demonstrated that, in the entire small intestine and the Peyer's patch which is the central tissue of the small intestine immunity, the expression level of the TGFβ gene was significantly lower in the synbiotics+anti-PD-1 antibody-administered group than in the Vehicle group, and thus suggested that the small intestine immunity was activated.

Example 5: Influence of In-Vivo Use of Synbiotics in Combination with Immune Checkpoint Inhibitor on Myeloid-Derived Suppressor Cells (MDSC) in Tumor Mouse colon cancer cell line MC38 cells were transplanted into 7-week-old male C57BL/6NCrSlc mice to produce cell line-transplanted model mice. They were divided into a control (Vehicle) group, a synbiotics-administered group, an anti-PD-1 antibody-administered group, and a synbiotics+anti-PD-1 antibody-administered group [n=10 (Vehicle group), n=5 (synbiotics-administered group and anti-PD-1 antibody-administered group), and n=6 (synbiotics+anti-PD-1 antibody-administered group)].

The synbiotics were orally administered at 0.2 mL/mouse once per day daily for 28 days after the transplantation, and the anti-PD-1 antibody was intraperitoneally administered from Day 7 after the tumor transplantation initially at 20 mg/kg and thereafter 10 mg/kg from the second to fourth time every 7 days.

At the time of dissection, the tumor was collected, and MDSCs were evaluated by real time PCR using Bv8 as an index (Mann Whitney U test).

Figure 5:
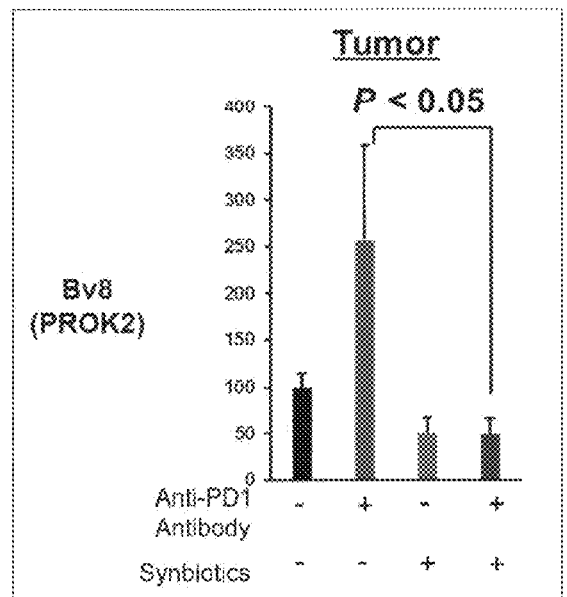
FIG. 5 shows the influence of synbiotics in combination with an immune checkpoint inhibitor on myeloid-derived suppressor cells (MDSC) in tumor.

FIG. 5 shows the results. Bv8 is a marker of MDSCs, and it is thus suggested that the number of MDSCs present in the tumor decreased, so that an antitumor effect was exerted.

Example 6: Influence of In-Vivo Use of Synbiotics in Combination with Immune Checkpoint Inhibitor in Systemic Immune Status Mouse colon cancer cell line MC38 cells were transplanted into 7-week-old male C57BL/6NCrSlc mice to produce cell line-transplanted model mice. They were divided into a control (Vehicle) group, a synbiotics-administered group, an anti-PD-1 antibody-administered group, and a synbiotics+anti-PD-1 antibody-administered group [n=10 (Vehicle group), n=5 (synbiotics-administered group and anti-PD-1 antibody-administered group), and n=6 (synbiotics+anti-PD-1 antibody-administered group)].

The synbiotics were orally administered at 0.2 mL/mouse once per day daily for 28 days after the transplantation, and the anti-PD-1 antibody was intraperitoneally administered from Day 7 after the tumor transplantation initially at 20 mg/kg and thereafter 10 mg/kg from the second to fourth time every 7 days.

At the time of dissection, each tissue (small intestine and tumor) was collected, and the expression level of each cytokine (IFN-β and IL-17) gene was evaluated by real-time PCR (Mann Whitney U test).

Figure 6:
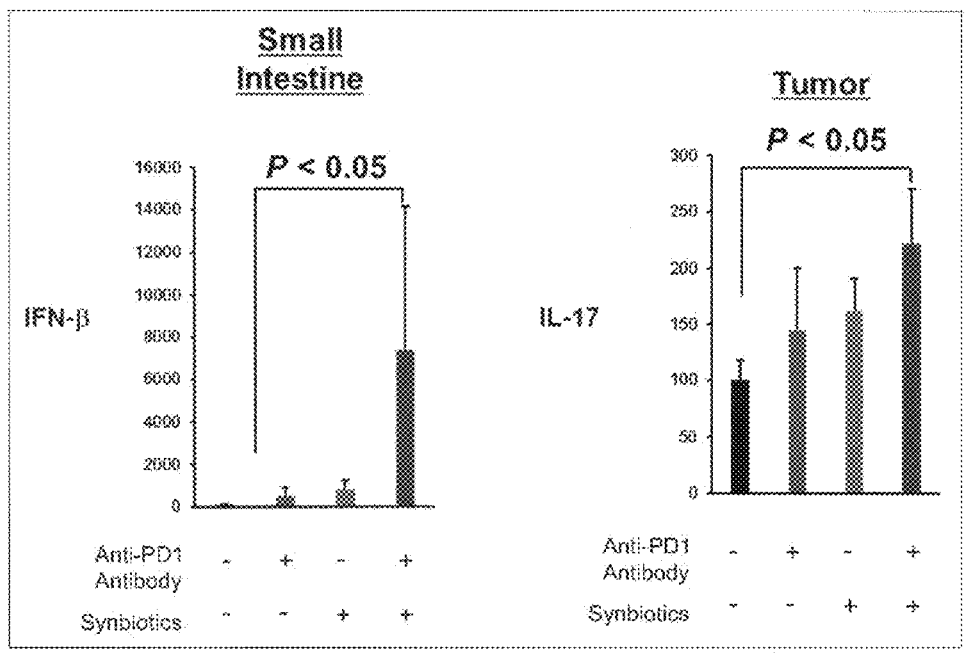
FIG. 6 shows the influence of synbiotics in combination with an immune checkpoint inhibitor on the immune status.

FIG. 6 shows the results. FIG. 6 revealed that the expression level of IFN-β gene which is an anti-inflammatory cytokine was high specifically in the small intestine of the synbiotics+anti-PD-1 antibody-administered group. In view of this result and the low value of TGFβ shown in FIG. 4, the immune function in the small intestine was highly possibly enhanced. Meanwhile, IL-17 is a cytokine which is highly expressed by immune cells, and its significantly high value in the synbiotics+anti-PD-1 antibody-administered group suggests an increase in immune cells in the tumor. Both of these results support the activation of tumor immunity.

Example 7: NK Cell Activity-Enhancing Action of In-Vivo Use of Various Intestinal Bacteria Formulations in Combination with Immune Checkpoint Inhibitor Mouse colon cancer cell line MC38 cells were transplanted into 7-week-old male C57BL/6NCrSlc mice to produce cell line-transplanted model mice. They were divided into a control (Vehicle) group (C), an anti-PD-1 antibody-administered group (P), a probiotics+anti-PD-1 antibody-administered group (LP), a prebiotics+anti-PD-1 antibody-administered group (GP), a synbiotics-administered group (LG), and a synbiotics+anti-PD-1 antibody-administered group (LGP) {n=9 (C, LG, and LGP) and n=8 (P, GP, and LP)}.

The synbiotics were orally administered at 0.2 mL/mouse in a cycle of once per day for 6 days excluding Sunday after the transplantation for 15 days in total, and the anti-PD-1 antibody was intraperitoneally administered from Day 6 after the tumor transplantation initially at 20 mg/kg and thereafter 10 mg/kg from the second to third time every 7 days. Single cells were prepared from the spleen collected at the time of dissection and used as effector cells. As the target cells, YAC-1 cells, which are mouse lymphomas, were used. The target cells ($4\times10^5$ cells/mL) were cultured at 37° C. for 30 minutes with calcein-acetoxymethylester (calcein-AM, a cell labeling reagent, at a final concentration of 1 mg/mL) added to perform fluorescent staining. The stained target cells ($1\times10^4$ cells/100 mL) and the pre-cultured effector cells ($4\times10^5$ cells/100 mL) were co-cultured in a U-bottom 96-well plate for 4 hours (effector cells:target cells=40:1). Then, after centrifugation at 300×g for 5 minutes, 80 μL of the supernatant was transferred to a black 96-well plate, and the amount of calcein-AM transferred to the culture supernatant was measured using a fluorescence plate reader (Ex. 488 nm and Em. 535 nm). The results obtained were applied to the following formula to calculate the cytotoxic activity (n=6, standard error, Dunnet's test).

Cytotoxic activity (% cytolysis)=((sample fluorescence intensity−spontaneous fluorescence intensity)×100)/(maximum fluorescence intensity−spontaneous fluorescence intensity)

Figure 7:
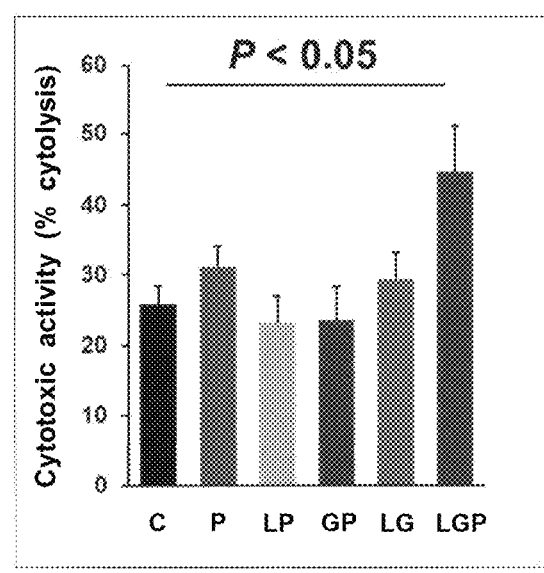
FIG. 7 shows NK cell activity-enhancing action of various intestinal bacteria formulations in combination with an immune checkpoint inhibitor. C: control group, P: anti-PD-1 antibody-administered group, LP: probiotics+anti-PD-1 antibody-administered group, GP: prebiotics+anti-PD-1 antibody-administered group, LG: synbiotics-administered group, and LGP: synbiotics+anti-PD-1 antibody-administered group.

FIG. 7 shows the results. From FIG. 7, it is understood that the cytotoxic activity of NK cells was significantly activated only in the LGP group including all three of the probiotics, the prebiotics, and the anti-PD-1 antibody. As a result of suppressing the anti-immune defense function of the tumor by the decrease of the number of Tregs shown in FIG. 2, the activity of immune cells on the tumor increased, which is a result supporting the activation of tumor immunity by the combined use of both formulations.

The invention claimed is:

1. A method for potentiating an antitumor effect of an immune checkpoint inhibitor, the method comprising:
   administering an effective amount of a probiotic, a prebiotic, and an immune checkpoint inhibitor to a subject in need thereof,
   wherein the probiotic comprises *Lactobacillus casei* YIT9029 (FERM BP-1366) and *Bifidobacterium breve* YIT12272 (FERM BP-11320),
   the prebiotic is a galactooligosaccharide, and
   the immune checkpoint inhibitor is an anti-PD-1 antibody.
2. The method of claim 1, wherein a content ratio of the probiotic to the prebiotic is from $0.01\times10^{11}$ to $20\times10^{11}$ CFU to 1 g of the total mass of the prebiotic.

* * * * *